United States Patent [19]

Croisier et al.

[11] 4,080,450
[45] Mar. 21, 1978

[54] 2-CARBAMOYL-1,2,4,5-TETRAHYDRO-3H-2-BENZAZEPIN-3-ONES

[75] Inventors: Paul Croisier, Waterloo; Ludovic Rodriguez, Brussels, both of Belgium

[73] Assignee: U C B, Societe Anonyme, Brussels, Belgium

[21] Appl. No.: 819,280

[22] Filed: Jul. 27, 1977

[30] Foreign Application Priority Data

Jul. 30, 1976 United Kingdom ............... 31845/76

[51] Int. Cl.² .................. C07D 223/16; C07D 413/06; A61K 31/55
[52] U.S. Cl. ............................. 424/244; 260/239.3 B; 424/248.54
[58] Field of Search ................. 260/239.3 B; 424/244, 424/248.54

[56] References Cited
PUBLICATIONS

Wittekind et al., "J. Het. Chem." vol. 8, pp. 495–501 (1971).

*Primary Examiner*—Henry R. Jiles
*Assistant Examiner*—Robert T. Bond
*Attorney, Agent, or Firm*—Wenderoth, Lind & Ponack

[57] ABSTRACT

New physiologically active 2-carbamoyl-1,2,4,5-tetrahydro-3H-2-benzazepin-3-ones having the general formula

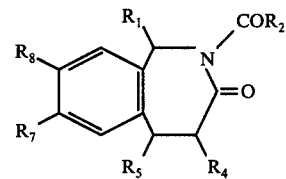

wherein $R_1$ is hydrogen or phenyl, $R_2$ is morpholino or amino mono- or di-substituted by $C_1$-$C_4$-alkyl, $C_5$-$C_6$-cycloalkyl or phenyl, $R_4$ is hydrogen or $C_1$-$C_4$-alkyl, $R_5$ is hydrogen or $C_1$-$C_4$-alkyl, $R_7$ is hydrogen, halogen or $C_1$-$C_4$-alkoxy, $R_8$ is hydrogen, halogen or $C_1$-$C_4$-alkyl, processes for the preparation thereof and pharmaceutical compositions containing the same. In particular, the compounds of this invention are useful in the treatment of memory disorders.

11 Claims, No Drawings

2-CARBAMOYL-1,2,4,5-TETRAHYDRO-3H-2-BENZAZEPIN-3-ONES

The present invention relates to new physiologically active 2-carbamoyl-1,2,4,5-tetrahydro-3H-2-benzazepin-3-ones, to processes for the preparation thereof and to pharmaceutical compositions containing the same.

The new 2-carbamoyl-1,2,4,5-tetrahydro-3H-2-benzazepin-3-ones according to the present invention are compounds of the general formula

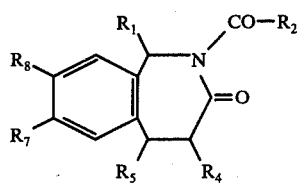

wherein $R_1$ is a hydrogen atom or a phenyl radical, $R_2$ is a morpholino radical or an amino group which is mono- or disubstituted by an alkyl radical containing 1 to 4 carbon atoms or a cycloalkyl radical containing 5 or 6 carbon atoms or a phenyl radical, $R_4$ is a hydrogen atom or an alkyl radical containing 1 to 4 carbon atoms, $R_5$ is a hydrogen atom or an alkyl radical containing 1 to 4 carbon atoms, $R_7$ is a hydrogen or halogen atom or an alkoxy radical containing 1 to 4 carbon atoms and $R_8$ is a hydrogen or halogen atom or an alkyl radical containing 1 to 4 carbon atoms.

The 1,2,4,5-tetrahydro-3H-2-benzazepin-3-one system (I), even when unsubstituted, is a recent acquisition in chemistry, because, although it was mentioned for the first time in 1949 as the product resulting from a Schmidt rearrangement of 3,4-dihydro-2(1H)-naphthalenone (see I.L. KNUNYANTS and B.P. FABRICHNYI, Doklady Akad.Nauk.S.S.S.R.,68,(1949),5-23-526)

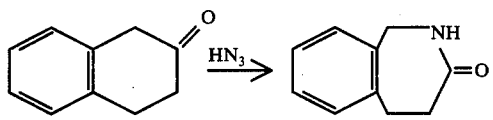

and was stated to have a melting point of 109°–110° C., after recrystallization from water, it has recently been proved that this product was actually a mixture of substances (A.N. KOST and A.P. STANKEVICIUS, Chem.Het.Compounds, 7,(9),(1971),1288–92). French Patent Specification No 1,472,930, which also deals with the same reaction, likewise gives, as the melting point, that of the mixture. It was not until the publication of the work of A.P. STANKEVICIUS and A.N. KOST (see Russian Patent Specification No 190,365 and the article by A.N. KOST and A.P. STANKEVICIUS, loc.cit.) that there was evidence of the application of a method of synthesis leading unambiguously to the desired lactam. This synthesis can be illustrated as follows:

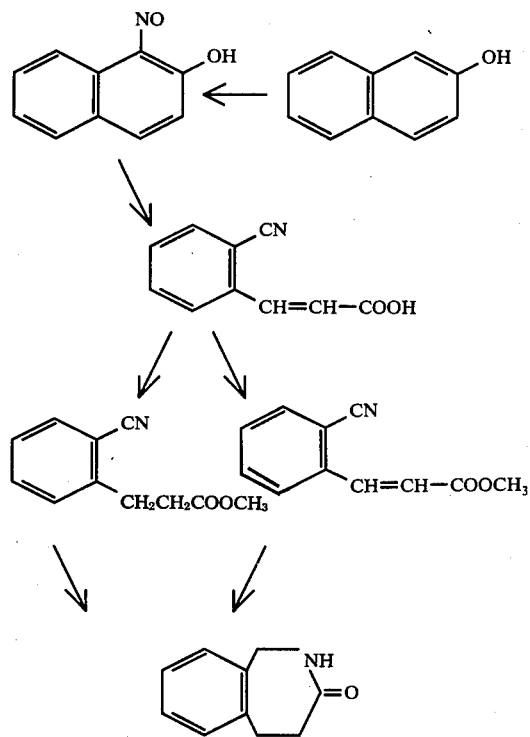

The 1,2,4,5-tetrahydro-3H-2-benzazepin-3-one thus obtained melts at 135°–136° C., after recrystallization from carbon tetrachloride.

The work of these Russian authors makes no mention of any substituted derivatives of the fundamental bicyclic system.

In 1958, H.A. BRUSON et al. (see J.Am.chem. Soc.80,(1958),3633–36) mention the probability of obtaining the 1,1,5,5-tetramethyl derivative, while in 1970 (P.C. MUKHARJI et al. (Indian J.Chem.,8,(1970),2-25–29 and ibid. 8,(1970),318–24) on the sole basis of carbon and hydrogen analyses, state that they isolated the following derivatives

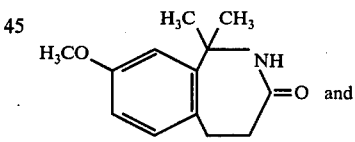

and

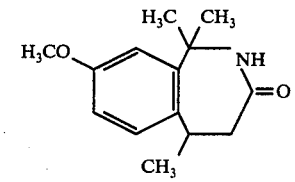

starting from the corresponding 3,4-dihydro-2(1H)-naphthalenones.

Structural proofs of the substituted products did not finally appear until the publication of the article by R.T. CONLEY et al. (J.Org.Chem.28,(1963),210–14) for the 1,1-dimethyl and 1,1,5,5-tetramethyl derivatives, which were also prepared from the corresponding 3,4-dihydro-2(1H)-naphthalenones and the more recent publication by R.R. WITTEKIND et al. (J.Het.-Chem.8,(1971),495–501) relating to five derivatives having methoxy radicals in both the 7- and 8-positions, which were prepared by reacting 3-(3,4-dimethoxyphenyl)-propionamide with benzaldehyde, s-trioxane and paraldehyde:

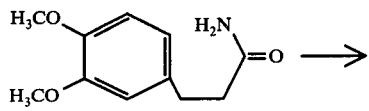

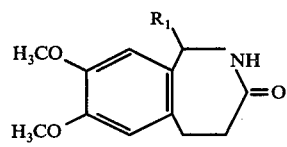

Furthermore, it is this last work that also mentions the isolation of the only N-substituted derivative known hitherto:

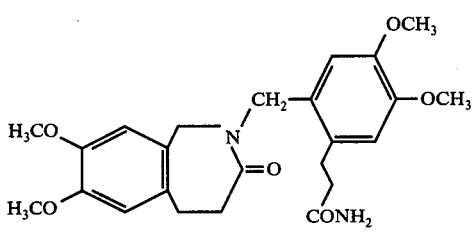

It was obtained in a yield of only 3% and was, in any case, produced unintentionally.

The absence of derivatives substituted in the 2- and 4-positions is also to be noted.

Furthermore, the pharmacological properties of the 1,2,4,5-tetrahydro-3H-2-benzazepin-3-ones synthesized in this way have not been examined by their authors, who generally prepared them as intermediates in the synthesis of the corresponding 2,3,4,5-tetrahydro-1H-2-benzazepines (see A.N. KOST et al., loc.cit.; and R.R. WITTEKIND et al., loc.cit.).

For the preparation of the compounds according to the present invention, it should be noted that the method used by the Russian authors starting from β-naphthol does not enable a substituent to be introduced in the 1-position and furthermore is of very little interest, in view of the different availability of the starting materials. On the other hand, WITTEKIND's method appears to be limited to phenylpropionamides with electrodonor radicals on the benzene ring.

The 2-carbamoyl-1,2,4,5-tetrahydro-3H-2-benzazepin-3-ones according to the present invention may be prepared by one of the following processes:

(a) A 1,2,4,5-tetrahydro-3H-2-benzazepin-3-one of formula (II) is reacted with an isocyanate of formula (III) in an appropriate solvent, if necessary in an autoclave, in accordance with the following equation:

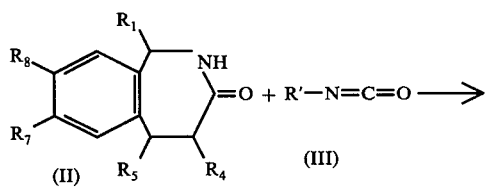

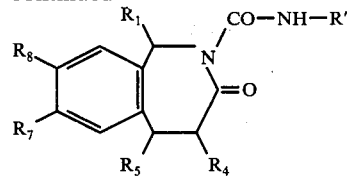

(I) wherein $R_2 = NH - R'$ wherein R' is an alkyl radical containing 1 to 4 carbon atoms or a cycloalkyl radical containing 5 or 6 carbon atoms or a phenyl radical and $R_1$, $R_4$, $R_5$, $R_7$ and $R_8$ have the same meanings as above.

(b) An alkali metal derivative of a 1,2,4,5-tetrahydro-3H-2-benzazepin-3-one of formula (IV) is reacted with an $R_2$-carbonyl halide according to the following equation:

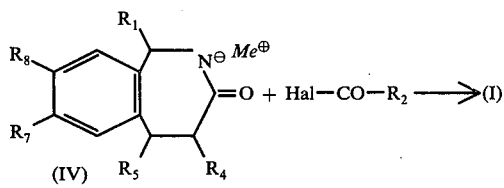

wherein $R_1$, $R_2$, $R_4$, $R_5$, $R_7$ and $R_8$ have the same meanings as above, Me is an alkali metal such as sodium or potassium and Hal is a halogen atom, such as chlorine or bromine.

The 1,2,4,5-tetrahydro-3H-2-benzazepin-3-ones used as starting materials in the preparation of the 2-carbamoyl compounds of the present invention, as well as methods of preparing them, are the subject matter of our Application filed concurrently herewith to which reference is made for a detailed description. They are also new compounds, except for 1,2,4,5-tetrahydro-3H-2-benzazepin-3-one (in which $R_1$, $R_2$, $R_4$, $R_5$, $R_7$ and $R_8$ are all hydrogen atoms), which has already been described in the literature (see I.L. KNUNYANTS et al., loc.cit.; and A.P. STANKEVICIUS et al., loc.cit.).

The compounds according to the present invention have valuable pharmaceutical properties and, in particular, have a beneficial action on mnemic processes and a protective action against hypoxic type aggressions. Thus, their first use is in geropsychiatry, a field which is characterized by disorders of the memory due not only to senile cellular alterations but also to a decrease in the supply of oxygen to the brain as a consequence of isolated or repeated vascular injuries (V.C. HACHINSKI, Lancet,II(1974). 207). Furthermore, the compounds according to the present invention are useful in many other clinical indications, for example, the prevention and treatment of cerebro-vascular or cardio-vascular injuries, post-traumatic or toxic comas, memory disorders, difficulties of mental concentration and the like.

Action on the mnemic processes is shown, in particular, by a reduction in the time for spinal fixation, a test which has been described in the literature (C. GIURGEA and F. MOURAVIEFF-LESUISSE, Arch.Int.-Pharmacodyn. 191,(2),(1971),279) as an elementary model of memory and which is endowed with a pharmacological reactivity in good correlation with the clinical physiopathology. In the rat, after unilateral lesion of the cerebellum, there is a postural asymmetry of the hind paws. This asymmetry may persist, even after spinal section, if the animal has been in this situation for a sufficiently long period of time. This time, which is called the spinal fixation time, is 45 minutes under the experimental conditions. On the other hand, if spinal section is performed before the expiry of this period, for example 35 minutes after the onset of the asymmetry, the latter disappears. Animals treated with placebos do not retain this asymmetry under these conditions. Conversely, any compound which allows the rats to retain the asymmetry (thus achieving spinal fixation) when the spinal section is carried out after 35 minutes, is regarded as being active.

Under these conditions, administration of a compound according to the present invention, for example 2-methyl-carbamoyl-1,2,4,5-tetrahydro-3H-2-benzazepin-3-one (compound A) or 4,5-dimethyl-2-methylcarbamoyl-1,2,4,5-tetrahydro-3H-2-benzazepin-3-one (compound B), produces the following effects:

Compounds A and B, administered intraperitoneally at a dose of 70 to 24 mg./kg., respectively (i.e. 0.3 and 0.1 mmole/kg.) produce spinal fixation after 35 minutes in three animals out of five and three animals out of seven, respectively.

Under the same conditions, piracetam is active at a dose of 30 mg./kg. (0.2 mmole/kg.) at which dose it causes spinal fixation in four animals out of nine (see C. GIURGEA and F. MOURAVIEFF-LESUISSE, loc.-cit.).

The action on mnemic processes is also demonstrated by the ability of the compounds to improve another type of memory retention in the rat. The principle of the active avoidance test, which has been developed in our laboratories and used for this purpose, may be described as follows: the withdrawal reaction of a rat's paw subjected to increasing and measured pressure is observed. The pressure at which the withdrawal reaction is produced is called the reaction threshold. The latter is expressed in grams and thus corresponds to the minimum pressure which, when applied to the paw of the animals causes withdrawal. It is read off directly from a scale on the apparatus used. When tested 24 hours later, the control animals exhibit no apparent retention of the earlier test: the avoidance is produced at an an intensity of stimulation comparable to that of the previous day. Conversely, animals treated with a compound which has a positive effect on the mnemic processes (for example, piracetam) show a significant degree of retention: the stimulus to which the rats react with reflex of avoidance is statistically lower than that for the control animals. A minimum of 20 rats are used for each test (10 treated rats and 10 control rats), the active dose being defined as the minimum dose which lowers the stimulus to below 110 g.

Subcutaneous administration of compounds according to the present invention, namely, 2-methylcarbamoyl-1,2,4,5-tetrahydro-3H-2-benzazepin-3-one (compound A), 4,5-dimethyl-2-methylcarbamoyl-1,2,4,5-tetrahydro-3H-2-benzazepin-3-one (compound B), 5-methyl-2-morpholinocarbonyl-1,2,4,5-tetrahydro-3H-2-benzazepin-3-one (compound C), 7-chloro-2-methylcarbamoyl-1,2,4,5-tetrahydro-3H-2-benzazepin-3-one (compound D), 7-chloro-4-methyl-2-methylcarbamoyl-1,2,4,5-tetrahydro-3H-2-benzazepin-3-one (compound E), 2-n-butylcarbamoyl-1,2,4,5-tetrahydro-3H-2-benzazepin-3-one (compound F), 2-n-butylcarbamoyl-7-methoxy-1-phenyl-1,2,4,5-tetrahydro-3H-2-benzazepin-3-one (compound G) and 2-dimethylcarbamoyl-1,2,4,5-tetrahydro-3H-2-benzazepin-3-one (compound H) produces under these conditions the effects set out in the following Table I. This Table I shows that the compounds according to the present invention exert, in this test, an activity which is superior to that of piracetam.

TABLE I

| Compound | Subcut. dose mg./kg. | Stimulus* | Active dose mg./kg. | Active dose mmole/kg. |
|---|---|---|---|---|
| A | 0 | 159 | | |
| | 1.09 | 120 | | |
| | 2.18 | 89 | 2.18 | 0.01 |
| B | 0 | 152 | | |
| | 0.49 | 124 | | |
| | 1.23 | 107 | 1.23 | 0.005 |
| C | 0 | 173 | | |
| | 0.28 | 116 | | |
| | 2.88 | 98 | 2.88 | 0.01 |
| D | 0 | 157 | | |
| | 1.26 | 122 | | |
| | 2.52 | 100 | 2.52 | 0.01 |
| E | 0 | 163 | | |
| | 0.26 | 115 | | |
| | 0.53 | 83 | 0.53 | 0.002 |
| F | 0 | 159 | | |
| | 0.2 | 92 | <0.2 | <0.0008 |
| G | 0.72 | 106 | 0.72 | 0.002 |
| | 3.66 | 95 | 3.66 | 0.01 |
| H | 2.32 | 90 | 2.32 | 0.01 |
| piracetam | 0 | 153 | | |
| | 1.5 | 120 | | |
| | 3.5 | 90 | 3.5 | 0.025 |

*Stimulus (expressed in g.) initiating the avoidance reaction 24 hours after the first stimulation.

Protection against hypoxic type aggressions, on the other hand, is demonstrated by a reduction in the lethality induced by a curarizing agent with a short duration of action, i.e. oxydipentonium chloride (Brevatonal). At the doses used, this curarizing agent brings about a respiratory depression which, in turn, brings about a hypoxi-hypercapnic syndrome. A compound capable of protecting the brain during this short period of hypoxia ensures survival. The compounds are administered to groups of 10 mice one hour before the injection of the curarizing agent; concurrently herewith, a control group of 10 mice is given a physiological salt solution prior to the curarizing agent. For each compound, the proportion of mice which survive is compared to the proportion of control mice which survive by the "Fisher exact probability test". This test, called the Brevatonal test, has also been developed in our laboratories.

Intraperitoneal administration (i.p.) of compounds according to the present invention, namely, 2-methylcarbamoyl-1,2,4,5-tetrahydro-3H-2-benzazepin-3-one (compound A), 4,5-dimethyl-2-methylcarbamoyl-1,2,4,5-tetrahydro-3H-2-benzazepin-3-one (compound B) and 4-n-butyl-2-methylcarbamoyl-1,2,4,5-tetrahydro-3H-2-benzazepin-3-one (compound I) under these conditions produced the effects summarized in the following Table II. It can be seen from this Table II that the compounds according to the present invention produce, at equal doses, an activity superior to that of piracetam.

TABLE II

| Compound | Dose mg./kg. (mmole/kg.) (i.p.) | Proportion of survivors | | Fisher exact probability |
|---|---|---|---|---|
| | | Treated animals | Control animals | |
| A | 70 (0.32) | 6/10 | 1/10 | P <0.05 |
| B | 25 (0.1) | 7/10 | 1/10 | P <0.025 |
| I | 27 (0.1) | 7/10 | 1/10 | P <0.025 |
| | 87 (0.32) | 8/10 | 1/10 | P <0.005 |
| piracetam | 45 (0.32) | 1/10 | 0/10 | not significant |
| | 142 (1) | 4/10 | 2/10 | not significant |

TABLE II-continued

| Compound | Dose mg./kg. (mmole/kg.) (i.p.) | Proportion of survivors | | Fisher exact probability |
|---|---|---|---|---|
| | | Treated animals | Control animals | |
| | 454 (3.2) | 8/10 | 1/10 | P <0.005 |

The new compounds according to the present invention appear to have a remarkably low toxicity. For example, for compound A, the lethal dose ($LD_{50}$) in the rat, when administered intraperitoneally, is more than 1000 mg./kg.

The new compounds according to the present invention may be administered orally, parenterally or rectally in admixture with pharmaceutical excipients or carriers.

Thus, in the case of oral administration, the forms used may be solid or liquid and may be presented, for example as gelatine capsules, coated or uncoated tablets, pills, solutions or suspensions in admixture with conventional pharmaceutical excipients or carriers. Examples of excipients for tablets include lactose, potato starch, corn starch, talc, gelatine, cellulose and cellulose derivatives, sugar, silica, stearic acid, magnesium stearate, calcium stearate, polyethylene glycols and polyvinylpyrrolidone, as well as various colorings and flavorings.

For parenteral administration, the excipient or carrier must be a parenterally acceptable sterile liquid, for example water or a solution of polyvinylpyrrolidone, or an oil, for example peanut oil.

For rectal administration, the excipient or carrier is usually a suppository base component, for example cocoa butter or a mixture of semiglycerides.

The forms of administration are advantageously in the form of appropriate dosage units. Tablets, pills, gelatine capsules, vials and suppositories preferably contain a unit dose of from 50 to 500 mg. Solutions and suspensions preferably contain from 1 to 20% by weight of an active compound according to the invention.

The following Examples are given for the purpose of illustrating the present invention, the chemical structure of all the compounds according to the present invention mentioned in the Examples having been confirmed by nuclear magnetic resonance, infra-red and mass spectrometry.

EXAMPLE 1

2-Methylcarbamoyl-1,2,4,5-tetrahydro-3H-2-benzazepin-3-one

A mixture of 8 g. (0.05 mole) of 1,2,4,5-tetrahydro-3H-2-benzazepin-3-one, 17 ml. (0.3 mole) of methyl isocyanate and 300 ml. of dry xylene is heated for 4 hours at 150° C. in a 500 ml. autoclave. The resultant solution is evaporated to dryness in vacuo and the residue is recrystallized twice from methanol. There are obtained 7.4 g. (65% of theory) of 2-methylcarbamoyl-1,2,4,5-tetrahydro-3H-2-benzazepin-3-one. M.P. 140°-141° C.

Analysis: $C_{12}H_{14}N_2O_2$ (M.W. 218.2) Calculated: C, 66.0%; H, 6.47%; N, 12.8%. Found: C, 65.9%; H, 6.45%; N, 12.9%.

The compounds set out in the following Table III are prepared in an analogous manner:

TABLE III

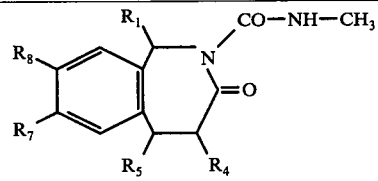

| $R_1$ | $R_4$ | $R_5$ | $R_7$ | $R_8$ | M.P. (recryst. solvent) | Yield % | Analyses calculated % | found % |
|---|---|---|---|---|---|---|---|---|
| $C_6H_5$ | H | H | $OCH_3$ | H | 167-168° C. (methanol) | 85 | $C_{19}H_{20}N_2O_3$ C 70.4 H 6.21 N 8.64 | (M.W. 324.4) 70.4 6.28 8.77 |
| H | $CH_3$ | H | H | H | 136-138° C. (methanol) | 60 | $C_{13}H_{16}N_2O_2$ C 67.2 H 6.94 N 12.1 | (M.W. 232.3) 67.3 6.92 12.1 |
| H | $C_2H_5$ | H | H | H | 124-125° C. (methanol) | 77 | $C_{14}H_{18}N_2O_2$ C 68.3 H 7.32 N 11.4 | (M.W. 246.3) 68.3 7.36 11.4 |
| H | $n-C_4H_9$ | H | H | H | 66-68° C. (isopropyl ether) | 40 | $C_{16}H_{22}N_2O_2$ C 70.1 H 8.03 N 10.2 | (M.W. 274.4) 70.1 8.10 10.2 |
| H | H | $CH_3$ | H | H | 104-105° C. (ethanol) | 56 | $C_{13}H_{16}N_2O_2$ C 67.2 H 6.94 N 12.1 | (M.W. 232.3) 67.2 6.96 12.1 |
| H | $CH_3$ | $CH_3$ (cis) | H | H | 99-100° C. (ethanol) | 75 | $C_{14}H_{18}N_2O_2$ C 68.3 H 7.36 N 11.4 | (M.W. 246.3) 68.3 7.40 11.3 |
| H | H | H | H | $CH_3$ | 159-160° C. (2-propanol) | 87 | $C_{13}H_{16}N_2O_2$ C 67.2 | (M.W. 232.3) 67.2 |

TABLE III-continued

[Structure: benzazepine with R1, R4, R5, R7, R8 substituents and CO—NH—CH3 group]

| R1 | R4 | R5 | R7 | R8 | M.P. (recryst. solvent) | Yield % | Analyses calculated % | found % |
|---|---|---|---|---|---|---|---|---|
| H | H | H | OCH3 | H | 132–133° C. (methanol) | 73 | H 6.94<br>N 12.1<br>$C_{13}H_{16}N_2O_3$ | 6.94<br>12.0<br>(M.W. 248.3) |
| H | CH3 | H | OCH3 | H | 150–151° C. (methanol) | 80 | C 62.9<br>H 6.45<br>N 11.3<br>$C_{14}H_{18}N_2O_3$ | 63.0<br>6.49<br>11.3<br>(M.W. 262.3) |
| H | H | H | Cl | H | 174–177° C. (methanol) | 77 | C 64.1<br>H 6.87<br>N 10.7<br>$C_{12}H_{13}ClN_2O_2$ | 64.2<br>6.91<br>10.7<br>(M.W. 252.5) |
| H | H | H | H | Cl | 172–173° C. (methanol) | 80 | C 57.1<br>H 5.15<br>N 11.1<br>$C_{12}H_{13}ClN_2O_2$ | 57.0<br>5.20<br>11.0<br>(M.W. 252.5) |
| H | CH3 | H | Cl | H | 160–161° C. (methanol) | 63 | C 57.1<br>H 5.15<br>N 11.1<br>$C_{13}H_{15}ClN_2O_2$ | 57.0<br>5.20<br>11.1<br>(M.W. 266.7) |
| H | C2H5 | H | Cl | H | 94–95° C. (methanol) | 32 | C 58.5<br>H 5.67<br>N 10.5<br>$C_{14}H_{17}ClN_2O_2$ | 58.6<br>5.72<br>10.4<br>(M.W. 280.7) |
| H | CH3 | H | H | Cl | 159–160° C. (methanol) | 47 | C 59.9<br>H 6.09<br>N 9.97<br>$C_{13}H_{15}ClN_2O_2$ | 59.8<br>6.13<br>9.90<br>(M.W. 266.7) |
|   |   |   |   |   |   |   | C 58.5<br>H 5.67<br>N 10.5 | 58.4<br>5.76<br>10.6 |

EXAMPLE 2

2-n-Butylcarbamoyl-1,2,4,5-tetrahydro-3H-2-benzazepin-3-one

A mixture of 8 g. (0.050 mole) of 1,2,4,5-tetrahydro-3H-2-benzazepin-3-one, 250 ml. of dry toluene and 5.5 g. (0.055 mole) of n-butyl isocyanate is heated under reflux for 4 hours. The resultant solution is evaporated to dryness in vacuo and the solid residue is recrystallized twice from diisopropyl ether. There are obtained 10.6 g. (81% of theory) of 2-n-butylcarbamoyl-1,2,4,5-tetrahydro-3H-2-benzazepin-3-one. M.P. 84.5° – 85° C.

Analysis: $C_{15}H_{20}N_2O_2$ (M.W. 260.3) Calculated: C, 69.3%; H, 7.69%; N, 10.8%. Found: C, 69.3%; H, 7.70%; N, 10.7%.

The compounds set out in the following Table IV are prepared in an analogous manner except that when R' is a cyclohexyl and phenyl radical, it is preferably to use xylene instead of toluene:

TABLE IV

[Structure: benzazepine with R1, R4, R5, R7, R8 substituents and CO—NH—R' group]

| R1 | R4 | R5 | R7 | R8 | R' | M.P. (recryst. solvent) | Yield % | Analyses calculated % | found % |
|---|---|---|---|---|---|---|---|---|---|
| H | n-C4H9 | H | H | H | iso-C3H7 | liquid | 75 | $C_{18}H_{26}N_2O_2$<br>C 71.5<br>H 8.66<br>N 9.26 | (M.W. 302.4)<br>70.0<br>8.6<br>9.3 |
| H | H | H | H | CH3 | n-C4H9 | 103–105° C. (methanol) | 67 | $C_{16}H_{22}N_2O_2$<br>C 70.0<br>H 8.08<br>N 10.2 | (M.W. 274.4)<br>70.1<br>7.87<br>10.6 |
| H | H | H | H | H | cyclohexyl | 100–101° C. (diisopropyl ether) | 77 | $C_{17}H_{22}N_2O_2$<br>C 71.3 | (M.W. 286.4)<br>71.2 |

TABLE IV-continued

[Structure: benzazepine with R_1, R_4, R_5, R_7, R_8 substituents and CO—NH—R' group]

| R_1 | R_4 | R_5 | R_7 | R_8 | R' | M.P. (recryst. solvent) | Yield % | Analyses calculated % | found % |
|---|---|---|---|---|---|---|---|---|---|
| H | CH_3 | H | H | H | cyclohexyl | 146–147° C. (methanol) | 74 | H 7.74<br>N 9.78<br>C_{18}H_{24}N_2O_2 | 7.82<br>9.74<br>(M.W. 300.4) |
| H | H | H | H | H | C_6H_5 | 135–136° C. (methanol) | 45 | C 72.0<br>H 8.05<br>N 9.32<br>C_{17}H_{16}N_2O_2 | 72.4<br>8.20<br>9.33<br>(M.W. 280.3) |
| H | CH_3 (cis) | CH_3 | H | H | C_6H_5 | 111–113° C. (methanol) | 58 | C 72.8<br>H 5.75<br>N 9.99<br>C_{19}H_{20}N_2O_2 | 73.1<br>5.80<br>10.1<br>(M.W. 308.4) |
| H | CH_3 | H | H | H | C_2H_5 | 79–80° C. (methanol) | 69 | C 74.0<br>H 6.54<br>N 9.08<br>C_{14}H_{18}N_2O_2 | 74.1<br>6.70<br>9.23<br>(M.W. 246.3) |
| H | n-C_4H_9 | H | H | H | n-C_4H_9 | 61–63° C. (acetone) | 64 | C 68.3<br>H 7.36<br>N 11.4<br>C_{19}H_{28}N_2O_2 | 67.6<br>7.02<br>10.6<br>(M.W. 316.4) |
| H | H | CH_3 | H | H | n-C_4H_9 | 82–84° C. (diisopropyl ether) | 57 | C 72.1<br>H 8.92<br>N 8.85<br>C_{16}H_{22}N_2O_2 | 72.1<br>8.90<br>8.82<br>(M.W. 274.3) |
| C_6H_5 | H | H | CH_3O | H | n-C_4H_9 | 119–20° C. (methanol) | 30 | C 70.0<br>H 8.08<br>N 10.2<br>C_{22}H_{26}N_2O_3 | 70.1<br>8.14<br>10.2<br>(M.W. 366.6) |
|  |  |  |  |  |  |  |  | C 72.1<br>H 7.14<br>N 7.64 | 72.1<br>7.12<br>7.60 |

EXAMPLE 3 cis-4,5-Dimethyl-2-morpholinocarbonyl-1,2,4,5-tetrahydro-3H-2-benzazepin-3-one 0.021 mole sodium hydride is added slowly, with stirring, to a solution of 3.3 g. (0.019 mole) of cis-4,5-dimethyl-1,2,4,5-tetrahydro-3H-2-benzazepin-3-one (prepared as indicated in Example 1 of our Application filed concurrently herewith) in 60 ml. of dimethylformamide, followed by heating at 80° C. for 30 minutes. After subsequently cooling in an ice bath, 3.2 g. (0.021 mole) of 4-morpholinecarbonyl chloride are added dropwise, the rate of addition being such that the temperature of the reaction mixture is kept at about 10° C. When the addition is complete, the temperature is slowly raised to 80° C. and then maintained at that level for 2 hours. The reaction mixture is subsequently evaporated to dryness in vacuo and the solid residue extracted with chloroform. The organic solution is washed twice with water, dried over anhydrous sodium sulfate and filtered and the filtrate then evaporated to dryness in vacuo. The solid residue is recrystallized from 2-propanol. There are obtained 3.8 g. (66% of theory) of cis-4,5-dimethyl-2-morpholinocarbonyl-1,2,4,5-tetrahydro-3H-2-benzazepin-3-one. M.P. 184°–185° C.

Analysis: C_{17}H_{22}N_2O_3 (M.W. 302.4) Calculated: C, 67.5%; H, 7.33%; N, 9.26%. Found: C, 67.4%; H, 7.40%; N, 9.20%.

The compounds set out in the following Table V are prepared in an analogous manner:

TABLE V

[Structure: benzazepine with R_5, R_8 substituents and CO—R_2 group]

| R_2 | R_5 | R_8 | M.P. (recryst. solvent) | Yield % | Analyses calculated % | found % |
|---|---|---|---|---|---|---|
| morpholino | CH_3 | H | 112–113° C. (ethanol) | 55 | C_{16}H_{20}N_2O_3<br>C 66.7<br>H 6.94<br>N 9.73 | (M.W. 288.3)<br>66.7<br>7.00<br>9.70 |

TABLE V-continued

[structure: benzazepine with R8, CO-R2, =O, R5 substituents]

| R₂ | R₅ | R₈ | M.P. (recryst. solvent) | Yield % | Analyses calculated % | found % |
|---|---|---|---|---|---|---|
| morpholino | H | CH₃ | 116–117° C. (ethanol + diisopropyl ether) | 27 | $C_{16}H_{20}N_2O_3$ (M.W. 288.3) C 66.7 H 6.94 N 9.73 | 66.4 7.10 9.60 |
| dimethylamino | H | H | 152–154° C. (diisopropyl ether) | 28 | $C_{13}H_{16}N_2O_2$ (M.W. 232.3) C 67.2 H 6.94 N 12.1 | 67.1 6.92 12.0 |

We claim:
1. A 2-carbamoyl-1,2,4,5-tetrahydro-3H-benzazepin-3-one having the formula

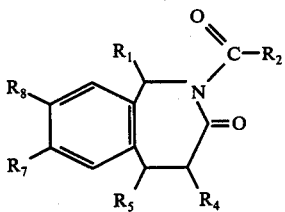

wherein
R₁ is a hydrogen atom or phenyl, R₂ is morpholino, or amino which is mono-or disubstituted by alkyl having 1 to 4 carbon atoms, cycloalkyl having 5 or 6 carbon atoms or phenyl,
R₄ is a hydrogen atom or alkyl having 1 to 4 carbon atoms,
R₅ is a hydrogen atom or alkyl having 1 to 4 carbon atoms,
R₇ is a hydrogen or halogen atom or alkoxy having 1 to 4 carbon atoms,
R₈ is a hydrogen or halogen atom or alkyl having 1 to 4 carbon atoms.

2. A compound as claimed in claim 1, namely 2-methylcarbamoyl-1,2,4,5-tetrahydro-3H-2-benzazepin-3-one.

3. A compound as claimed in claim 1, namely 4,5-dimethyl-2-methylcarbamoyl-1,2,4,5-tetrahydro-3H-2-benzazepin-3-one.

4. A compound as claimed in claim 1, namely 5-methyl-2-morpholinocarbonyl-1,2,4,5-tetrahydro-3H-2-benzazepin-3-one.

5. A compound as claimed in claim 1, namely 7-chloro-2-methylcarbamoyl-1,2,4,5-tetrahydro-3H-2-benzazepin-3-one.

6. A compound as claimed in claim 1, namely 7-chloro-4-methyl-2-methylcarbamoyl-1,2,4,5-tetrahydro-3H-2-benzazepin-3-one.

7. A compound as claimed in claim 1, namely 2-n-butylcarbamoyl-1,2,4,5-tetrahydro-3H-2-benzazepin-3-one.

8. A compound as claimed in claim 1, namely 2-n-butylcarbamoyl-7-methoxy-1-phenyl-1,2,4,5-tetrahydro-3H-2-benzazepin-3-one.

9. A compound as claimed in claim 1, namely 2-dimethylcarbamoyl-1,2,4,5-tetrahydro-3H-2-benzazepin-3-one.

10. A compound as claimed in claim 1, namely 4-n-butyl-2-methylcarbamoyl-1,2,4,5-tetrahydro-3H-2-benzazepin-3-one.

11. A composition having a beneficial activity on the mnemic processes and a protective activity against hypotoxic type aggressions comprising an effective amount for said uses of a 2-carbamoyl-1,2,4,5-tetrahydro-3H-2-benzazepin-3-one having the formula

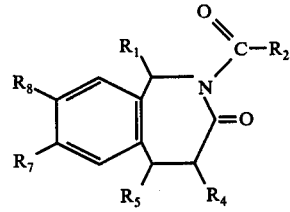

wherein
R₁ is a hydrogen atom or phenyl,
R₂ is morpholino, or amino which is mono-or disubstituted by alkyl having 1 to 4 carbon atoms, cycloalkyl having 5 or 6 carbon atoms or phenyl,
R₄ is hydrogen or alkyl having 1 to 4 carbon atoms,
R₅ is a hydrogen atoms or alkyl having 1 to 4 carbon atoms,
R₇ is a hydrogen or halogen atom or alkoxy having 1 to 4 carbon atoms,
R₈ is a hydrogen or halogen atom or alkyl having 1 to 4 carbon atoms, in admixture with a pharmaceutically acceptable solid or liquid carrier.

* * * * *

UNITED STATES PATENT OFFICE
CERTIFICATE OF CORRECTION

Patent No. 4,080,450  Dated March 21, 1978

Inventor(s) Paul Croisier and Ludovic Rodriguez

It is certified that error appears in the above-identified patent and that said Letters Patent are hereby corrected as shown below:

Claim 1, line 1, after "3H-" insert -- 2- --.

Claim 11, line 3, change "hypotoxic" to -- hypoxic --.

Signed and Sealed this

Twenty-seventh Day of February 1979

[SEAL]

Attest:

RUTH C. MASON
Attesting Officer

DONALD W. BANNER
Commissioner of Patents and Trademarks